United States Patent [19]

Schellenbaum et al.

[11] 4,025,556
[45] May 24, 1977

[54] QUATERNARY AMMONIUM-HYDROXYARYL COMPOUNDS

[75] Inventors: Max Schellenbaum, Muttenz; Max Dünnenberger, Frenkendorf, both of Switzerland

[73] Assignee: Ciba-Geigy AG, Basel, Switzerland

[22] Filed: May 22, 1975

[21] Appl. No.: 579,999

Related U.S. Application Data

[63] Continuation-in-part of Ser. No. 229,172, Feb. 24, 1972, abandoned, which is a continuation of Ser. No. 765,688, Oct. 7, 1968, abandoned.

[30] Foreign Application Priority Data

Oct. 16, 1967 Switzerland ............... 14446/67

[52] U.S. Cl. .............. 260/567.5; 260/567.6 M; 260/295 N; 260/290 R; 424/329; 260/286 Q
[51] Int. Cl.² ......................... C07C 93/06
[58] Field of Search ............... 260/567.6 M, 567.5

[56] References Cited

UNITED STATES PATENTS

| | | | |
|---|---|---|---|
| 2,427,658 | 9/1947 | Coleman et al. | 260/567.5 |
| 2,541,816 | 2/1951 | Glarum et al. | 260/567.5 |
| 2,821,488 | 1/1958 | Jezl | 260/567.6 |
| 3,284,407 | 11/1966 | Winfield et al. | 260/567.6 |

FOREIGN PATENTS OR APPLICATIONS 566,930 12/1958 Canada ............... 260/567.6

*Primary Examiner*—James O. Thomas, Jr.
*Assistant Examiner*—James H. Reamer
*Attorney, Agent, or Firm*—Karl F. Jorda; Edward McC. Roberts; Prabodh I. Almaula

[57] ABSTRACT

The present invention is concerned with quaternary ammonium-hydroxyaryl compounds of the formula

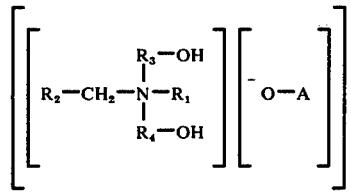

in which $R_1$ represents an aliphatic residue of high molecular weight, $R_2$ a monocyclic benzene residue, $R_3$ and $R_4$ each represents a short-chain divalent aliphatic residue and A an aromatic residue which contains at most 2-six-membered rings and is linked through a cyclic carbon atom with the oxygen atom. The new compounds are useful for controlling harmful microorganisms.

8 Claims, No Drawings

QUATERNARY AMMONIUM-HYDROXYARYL COMPOUNDS

This is a continuation-in-part of our patent application Ser. No. 229,172, filed Feb. 24, 1972, which in turn is a continuation of our patent application Ser. No. 765,688, filed Oct. 7, 1968 bath applications now abandoned.

The present invention is concerned with quaternary ammonium-hydroxyaryl compounds of the formula

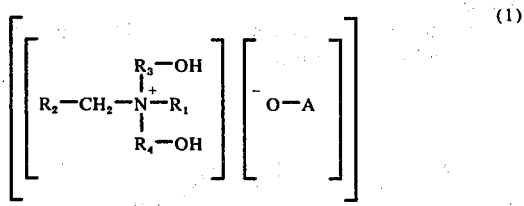

(1)

in which $R_1$ represents an aliphatic residue of high molecular weight, $R_2$ a monocyclic benzene residue, $R_3$ and $R_4$ each represents a short-chain divalent aliphatic residue and A an aromatic residue which contains at most 2-six-membered rings and is linked through a cyclic carbon atom with the oxygen atom.

The aromatic residue A, which be for instance a benzene, naphthalene or quinoline residue, may contain further substituents or it may be unsubstituted.

Preferred quaternary ammonium-hydroxyaryl compounds correspond to the formula

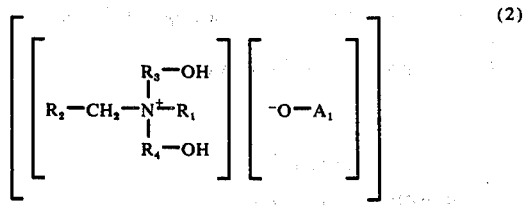

(2)

in which $R_{1-14\ 4}$ have the above meanings and $A_1$ represents an aromatic residue which contains at most 2 six-membered rings and is substituted by at least one halogen atom, which residue is linked through a cyclic carbon atom with the oxygen atom.

Other preferred quaternary ammonium hydroxyaryl compounds correspond to the formula

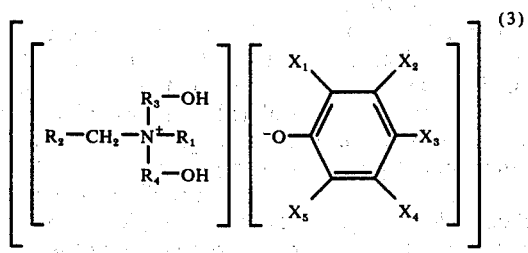

(3)

in which $R_{1-4}$ have the above meanings and $X_{1-5}$ each represents a halogen or hydrogen atom or an alkyl group which preferably contains 1 to 4 carbon atoms, and, furthermore, at most once 2 vicinal X-residues together may form the complement to a fused-on benzene or pyridine ring or at most 1 residue X is a benzene residue bound directly through a carbon or hetero atom with the ring of the phenolate ion. If the residues X are exclusively alkyl group or halogen or hydrogen atoms, the residue A is, accordingly, represented by benxene residues. As residues with fused-on rings there are suitable, for example, naphthalene, quinoline or quinaldine residues. If one of the residues X is a benzene residue bound directly through a carbon or hetero atom with the ring of the phenolate ion, the residues are, for example, diphenyl, diphenyl ether or diphenylmethane residues, all of which may be further substituted.

Particularly valuable compounds of the formula (3) correspond to the formula

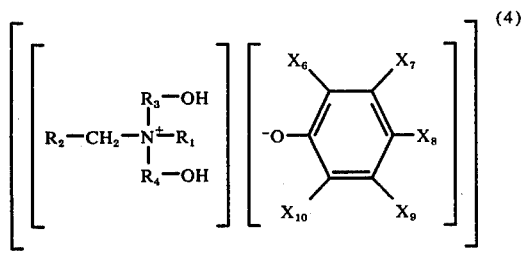

(4)

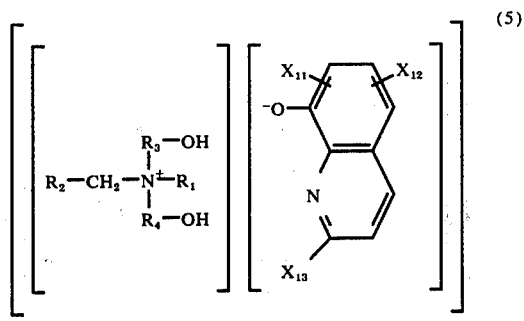

(5)

or

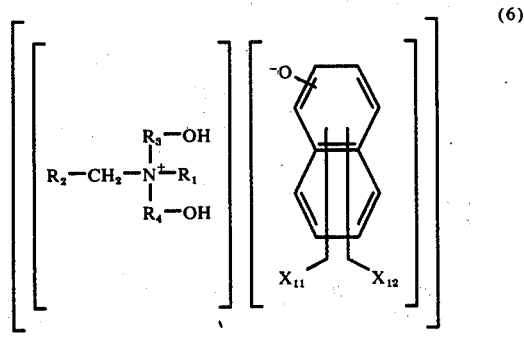

(6)

in which $R_{1-4}$ have the above meanings; at least one of the residues $X_{6-10}$ is a halogen atom; at most 2 of the residues $X_{6-10}$ are alkyl groups with 1 to 4 carbon atoms and the others represent a hydrogen atom each; $X_{11}$ and $X_{12}$ represent a hydrogen or halogen atom each and $X_{13}$ is a methyl group or preferably a hydrogen atom. The halogen atoms in the formulae (4(, (5) and (6) are preferably iodine, bromine or especially chlorine.

Compounds of formula (4) of very particular interest are such wherein one to three of the residues $X_{6-10}$ are halogen, at most two of the residues $X_{6-10}$ are alkyl groups with 1 to 4 carbon atoms and the remaining $X_{6-10}$ represents hydrogen.

Of special value are quaternary ammonium-hydroxyaryl compounds of the formulae

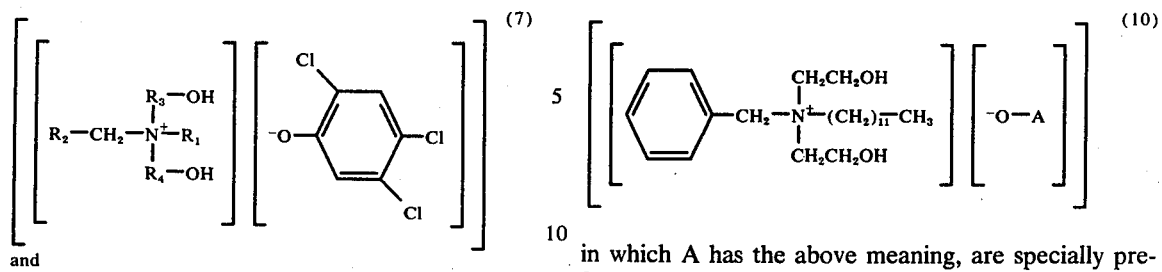

and

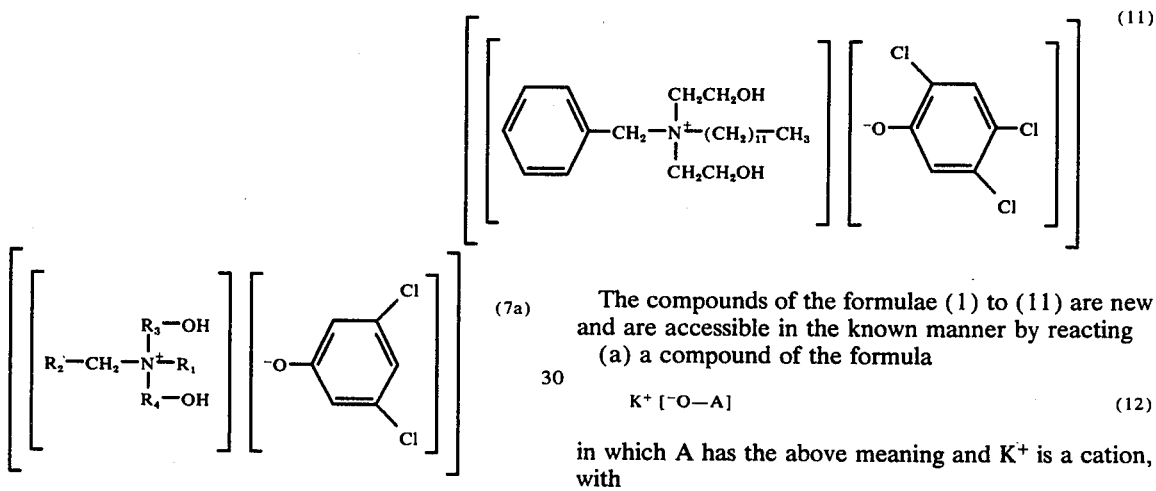

in which $R_{1-4}$ have the above meanings.

Specially suitable are also quaternary ammonium compounds of the formula

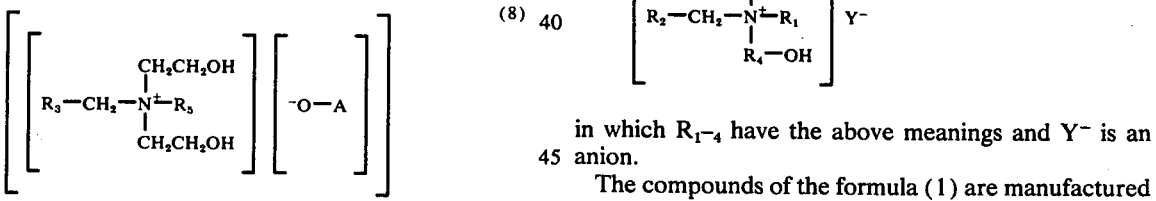

in which $R_5$ represents an alkyl residue containing 8 to 22, preferably 10 to 18 carbon atoms, and $R_2$ and A have the meanings defined above. Of very special importance are $R_5$ residues containing 12 to 16 carbon atoms, and among them in the first place quaternary ammonium compounds of the formula

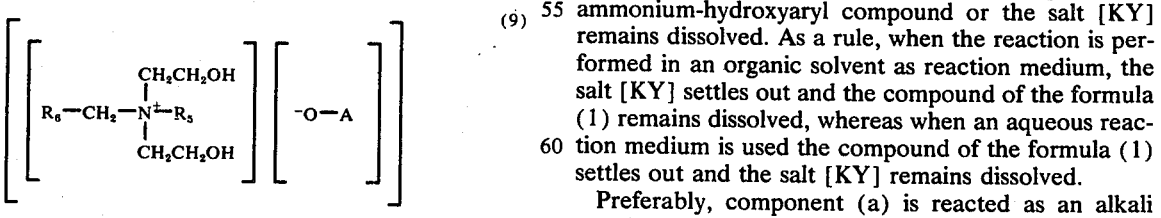

in which $R_6$ represents a benzene residue substituted by halogen atoms or alkyls with 1 to 4 carbon atoms, and $R_5$ and A have the meanings defined above.

Among these compounds the quaternary ammonium-hydroxyaryl compounds of the formula

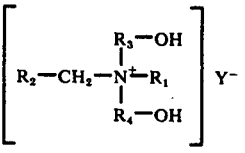

in which A has the above meaning, are specially preferred.

Specially good results have been obtained with the compound of the formula

The compounds of the formulae (1) to (11) are new and are accessible in the known manner by reacting
(a) a compound of the formula $$K^+ [^-O-A] \qquad (12)$$

in which A has the above meaning and $K^+$ is a cation, with
(b) a compound of the formula in which $R_{1-4}$ have the above meanings and $Y^-$ is an anion.

The compounds of the formula (1) are manufactured in an organic or advantageously aqueous solution heated at 20° to 80° C. The final products are in general colourless crystals. The reaction medium, as well as the cation $K^+$ and the anion $Y^-$ of the starting products, must in each case be chosen so that either the salt [KY] or the quaternary ammonium-hydroxyaryl compound of the formula (1) is isolated as an insoluble product from the reaction mixture and either the quaternary ammonium-hydroxyaryl compound or the salt [KY] remains dissolved. As a rule, when the reaction is performed in an organic solvent as reaction medium, the salt [KY] settles out and the compound of the formula (1) remains dissolved, whereas when an aqueous reaction medium is used the compound of the formula (1) settles out and the salt [KY] remains dissolved.

Preferably, component (a) is reacted as an alkali metal salt with a halide of component (b). Preferred halogen atoms are chlorine or bromine atoms, and the alkali metals salts are primarily sodium or potassium salts of pentachlorophenol.

To manufacture the compounds of the formulae (2) to (7a).

(a) a compound of the formulae $K_1^+ \; [\;^-O-A_1\;]$ (14)

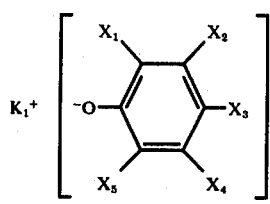 (15)

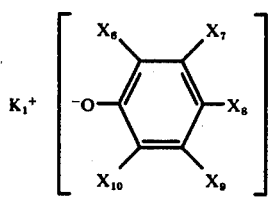 (16)

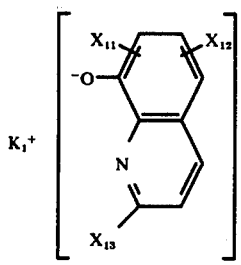 (17)

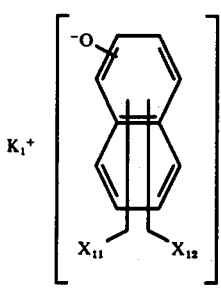 (18)

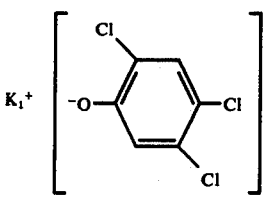 (19)

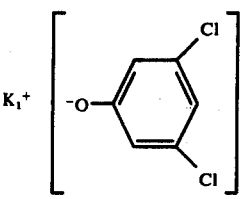 (19a)

in which $A_1$ and $X_{1-13}$ have the identical meanings and $K_1$ represents an alkali metal atom, is reacted with
(b) a compound of the formula

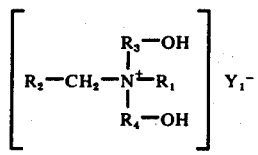 (20)

in which $R_{1-4}$ have the meanings defined above and $Y_1$ represents a halogen atom.

The monocyclic benzene residue of the starting compound of the formula (20) may be unsubstituted or substituted, preferably by halogen atoms or alkyls with 1 to 4 carbon atoms. $R_2$ in the formulae (1) to (8) and (20), and $R_6$ in the formula (9) respectively, may thus be, for example, a 4-chlorophenyl, 3,4-dichlorophenyl or 4-methylphenyl residue.

Accordingly, the compounds of the formulae (8) to (10) are obtained by reacting
(a) a compound of the formula $K_1^+ \; [\;^-O-A\;]$ (21)

in which $K_1$ and A have the above-defined meanings, with
(b) a compound of one of the formulae

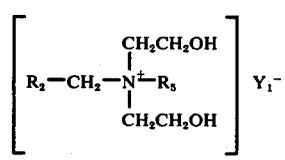 (22)

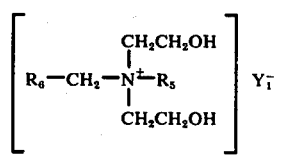 (23)

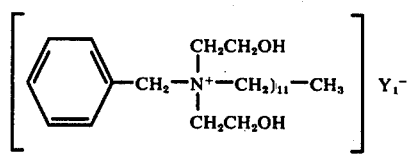 (24)

in which the residues $R_{1-6}$ have the above meanings and $Y_1$ represents a halogen atom.

The specially preferred compound of the formula (11) is obtained by reacting sodium trichlorophenolate with benzyl-bis-(2-hydroxyethyl)-dodecyl ammonium chloride.

The compounds of the formula (1) may be used for controlling harmful microorganisms, and these quaternary ammonium compounds may be incorporated in known manner in preparations which may be used in the usual manner for controlling harmful microorganisms. An especially valuable feature of the new agents is their broad antibacterial activity spectrum which includes both Gram-positive and Gram-negative bacteria. In this application the absence of odours and colours in the compounds of the formula (1) is of special value for their use. Accordingly, the present invention includes also their use in pest control quite generally. The new products may be used on a very broad basis, especially for protecting organic substrates from infestation by destructive and pathogenic (including phytopathogenic) microorganisms. Thus, the new compounds of the formula (1) are suitable for use as preservatives and disinfectants for textile materials and industrial products of all kinds, in plant protection, in agriculture, in veterinary medicine and in cosmetics.

From among industrial products that can be preserved with the aid of compounds of the formula (1) there may be mentioned, for example: Textile adjuvants and improving agents, glue, binders, paints, dye pastes and printing inks and similar preparations based on organic or inorganic dyestuffs or pigments, including those which contain a share of casein or other organic compounds. Wall and ceiling paints, for example those containing a proteinic colour binder, are likewise protected from infestation by pests by the addition of the new compounds. Timber may likewise be protected.

Furthermore, the compounds of the formula (1) may be used for a preserving and disinfectant finish on fibres and textile materials, including both natural and synthetic fibres, on which they produce a durable protective effect against harmful (including pathogenic) organisms, for example fungi and bacteria. Such an addition may be made before, during or after a treatment of the said textiles with other substances, for example dye pastes or printing inks, dressings or the like.

Textile materials treated in the said manner are also protected from the appearance of perspiration odour caused by microorganisms.

The compounds of the formula (1) may also be used as preservatives in the cellulose and paper industries, inter alia for preventing the known slime formation caused by microorganisms in the paper-making machines.

Furthermore, when compounds of the formula (1) are combined with detergent or surfactive substances there are obtained detergents and cleaning preparations having an excellent antibacterial or antimycotic activity. The compounds of the formula (1) may be incorporated, for example, with soaps, or combined with soap-free detergents or surfactant substances or with mixtures of soaps and soap-free detergents, and in such combinations their antimicrobial activity is fully retained.

Cleaning agents containing a compound of the formula (1) may be used in industry and in the home, also in the food industry, for example in dairies, breweries and abattoirs. The compounds of the formula (1) may also be used as ingredients of preparations used in cleaning or disinfecting.

Their activity may also be utilized in preserving and disinfectant finishes on synthetic materials. When plasticizers are used it is advantageous to add the compound of the formula (1) in form of a solution or dispersion in the plasticizer to the synthetic material. It is advantageous to ensure as even a distribution as possible in the synthetic material. Synthetics having antimicrobial properties may be used for utilitarian objects of all kinds that are desired to display an activity against a wide variety of germs, for example bacteria and fungi, thus for instance in doormats, bathroom curtains, seats, treads in swimbaths, or wall coverings. When they are incorporated with waxes or polishes floor polishes and furniture polishes having a disinfectant activity are obtained.

The compounds of the formula (1) can be applied to the material, such as textile material, to be protected in a variety of ways, for example by impregnation or spraying with solutions or suspensions containing the said compounds as active ingredients, or successive impregnation or spraying with solution of the starting compounds required for the manufacture of the active substances, the active substance being formed in situ on the material to be protected. Depending on the purpose in hand the content of active ingredient may vary from 1 to 30 g of active substance per liter of treatment liquor. In most cases textile material of synthetic or natural origin are sufficiently protected from infestation by fungi and bacteria by a content from 0.1 to 3% of active substance. The active substance may be used in combination with other textile adjuvants such as dressing agents, anti-crease finishes or the like.

The new products may be used in the formulations conventionally used for pesticides; for example, preparations containing a compound of the formula (1) may, if desired, further contain additives such as solvents, dispersants or adhesives, as well as other pesticides. Finally, such preparations for controlling harmful microorganisms may also contain several compounds of the formula (1) side by side. More especially, in addition to the active ingredient of the formula (1), the preparations may contain a solid or liquid diluent or a solid or liquid vehicle.

Unless otherwise indicated, parts and percentages in the following Examples are by weight.

EXAMPLE 1

The compound A of Table I may be prepared by one of the following two methods:

a. While vigorously stirring an aqueous solution of 28.8 parts of sodium pentachlorophenolate [prepared from 26.6 parts of pentachlorophenol, 4.0 parts of sodium hydroxide and 200 parts of water] at 25° C, it is mixed with a solution of 40.0 parts of benzyl-bis-(2-hydroxyethyl)-dodecyl ammonium chloride in 100 parts of water. The reaction mixture — from which the compound of the formula (11) has settled out in form of an oil — is stirred on for 2 hours and the product is then extracted with ethyl acetate. When petroleum ether is added to the concentrated ethyl acetate solution, pure benzyl-bis-(2-hydroxyethyl)-dodecyl ammonium pentachlorophenolate ( compound A) settles out in form of colourless crystals. Yield: 48 to 50 parts, melting at 87°–88° C.

b. A mixture of sodium pentachlorophenolate from 26.6 parts of pentachlorophenol and 4.0 parts of sodium hydroxide in 80 parts by volume of methanol is mixed at 60° C with 40.0 parts of benzyl-bis-(2-hydroxyethyl)dodecyl ammonium chloride in 30 parts by volume of methanol. The solvent is then distilled off and the residue taken up in 200 parts by volume of carbon tetrachloride. The sodium chloride (58 parts) is filtered off and the solution cooled in an ice bath, whereupon benzyl-bis-(2-hydroxyethyl)-dodecyl ammonium pentachlorophenolate settles out in the form of colourless crystals melting at 85°–86° C. Yield: about 54 parts.

In an analogous manner the compounds B to J in the following Table I may be prepared. In Table I column I lists the compound and column II its melting point in ° C.

TABLE I

| | $R_2$ | –O–A | m.p. (°C) |
|---|---|---|---|
| A | H | 2,3,4,5,6-pentachlorophenoxy | 87 to 88 |
| B | H | 2,3,4,5-tetrachlorophenoxy | 84.5 to 85.5 |
| C | H | 2,4,5-trichlorophenoxy | 105.5 to 106.5 |
| D | H | 2-chloro-3-methylphenoxy | 109 to 110 |
| E | H | 4-chloro-3,5-dimethylphenoxy | 119 to 120 |
| F | H | 2,2'-methylene-bis(3,4,6-trichlorophenoxy) | 110 to 111 |
| G | H | 2,5-dichlorophenoxy | 110 to 112 |
| | | (TABLE I-continued) | |
| | $R_2$ | –O–A | m.p. (°C) |
| | | 2-naphthoxy | 106.5 to 107.5 |
| H | Cl | 2,3,4,5-tetrachlorophenoxy | 92 to 93 |
| I | Cl | 2,4,5-trichlorophenoxy | 130 to 131 |
| J | –CH$_3$ | 2,4,5-trichlorophenoxy | 124.5 to 125.5 |

General structure (I and II):

$$\left[ R_2-C_6H_4-CH_2-N^+(CH_2CH_2OH)_2(C_{12}H_{25}) \right] \left[ -O-A \right]$$

EXAMPLE 2

The procedure described in Example 1 furnishes also the compound K of the formula

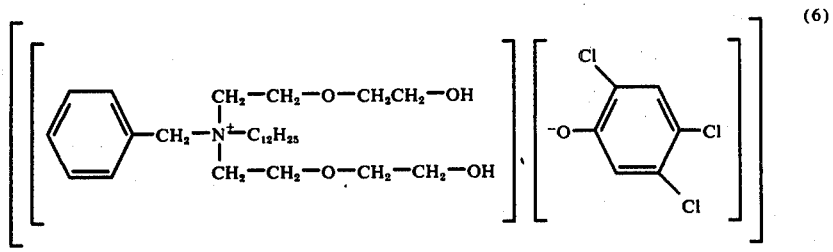

(6)

as a colourless oil.

EXAMPLE 3

14.5 parts of 8-hydroxyquinoline in 100 parts by volume of methylcellosolve (ethyleneglycol monomethyl ether) are converted with 4.0 parts of sodium hydroxide into the sodium salt, which is mixed at 55° to 60° C with a solution of 40.0 parts of benzyl-bis-(2-hydroxyethyl)-dodecyl ammonium chloride in 100 parts of water. The clear reaction solution is cooled to 25° C, whereupon the compound L of the formula

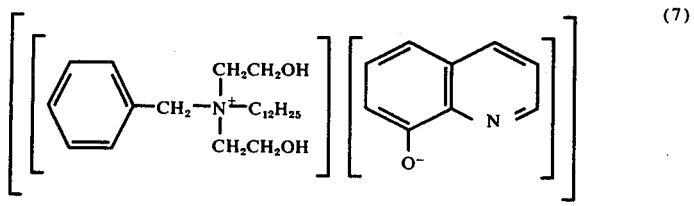
(7)

first settles out as an oil which crystallizes on standing. The product is filtered off, washed with water and dried. Yield: 45 parts. Melting point: 129° to 130.5° C. After recrystallization from methanol+ethyl acetate the product melts at 130° to 131° C.

In an analogous manner the compounds L to P in Table II are obtained. In Table II column I lists the compound and column II its melting point in ° C.

TABLE II

| I | | | II | |
|---|---|---|---|---|
| | $R_2$ | ⁻O—A | | |
| L | H | (8-quinolinolate) | | 130 to 131 |
| M | H | (5-chloro-8-quinolinolate) | | 129 to 130 |
| N | H | (5,7-dichloro-8-quinolinolate) | | 95 to 97 |
| O | H | (5,7-dibromo-8-quinolinolate) | | 106.5 to 108 |
| P | H | (5-chloro-7-iodo-8-quinolinolate) | | 85 to 87 |

Structure in I: $[R_2-C_6H_4-CH_2-N^+(CH_2CH_2OH)_2(C_{12}H_{25})]$ with counterion $^-O-A$

EXAMPLE 4

MEASURING THE MINIMAL INHIBITORY CONCENTRATION (MIC) AGAINST BACTERIA AND FUNGI IN THE DILUTION TEST

The minimal inhibitory concentration (MIC) is measured by a test derived from standardized methods which makes available an approximation to absolute minimal inhibitory values of an active substance.

A solution of 0.4% and 0.12% strength each in dimethylsulphoxide is prepared with the active substances. 0.25 ml of each of these solutions is added to 9.75 ml of sterile brain heart infusion broth (bacteria) and beerwort solution (fungi) respectively. By continual dilution to 10 times the volume two series are obtained which are combined and thereby converted into the following continuous dilution series:

100, 30, 10, 3, 1 . . . part per million of active substance.

The solutions are inoculated with the bacterium *Staphylococcus aureus* and with fungi *Aspergillus niger* and *Rhizopus nigricans* respectively. Then incubation is performed for 48 hours at 37° C (bacteriostasis) with *Staphylococcue aureus* and for 72 hours at 30° C (fungistasis) with the fungi.

After the times indicated the minimal inhibitory values in parts per million shown in the following Table were recorded:

TABLE III

| Compound of formula No | Inhibitory values in ppm in | | |
|---|---|---|---|
| | bacteriostasis Staphylococcus aureus | fungistasis Aspergillus niger | Rhizopus nigricans |
| (11) | 10 | 10 | 10 |

EXAMPLE 5

MEASURING THE MINIMAL INHIBITORY CONCENTRATION (MIC) TOWARDS BACTERIA AND FUNGI IN THE GRADIENT PLATE TEST

The compounds of the formula (1) in suitable formulations (for example as solutions in dimethylsulphoxide) of certain concentrations are mixed with warm brain heart infusion agar (bacteria) and *Mycophil-Agar* (fungi). The liquid mixtures are poured over a solidified, wedge-shaped basic agar layer and likewise allowed to solidify.

The test organisms are then applied by means of a Pasteur pipette in lines at right angles to the gradient. After an incubation period of 24 hours at 37° C (bacteria) and 72 hours at 30° C (fungi) the length of the germs grown on the inoculation line is measured and expressed in parts per million of active substance.

TABLE IV

| Compound | Minimal inhibitory concentration (ppm) | | | |
|---|---|---|---|---|
| | Bacteriostasis | | Fungistasis | |
| | Staphylococcus aureus | Escherichia coli | Aspergillus niger | Trichophyton mentagrophytes |
| L | 3 | 20 | 6 | 6 |
| B | 4 | >100 | 5.5 | 1.5 |
| C | 3 | 20 | 5 | 1 |
| D | 3 | 20 | 7.5 | 10 |
| E | 2 | >100 | 6 | 5.5 |
| F | 0.3 | >100 | >100 | >100 |
| G | 3 | 20 | 7 | 10 |
| H | 2 | >100 | 10 | 1 |
| I | 2 | 25 | 5 | 1 |
| K | 10 | 30 | 20 | 5 |
| J | 2 | 20 | 4 | 2 |
| M | 3 | 30 | 10 | — |
| N | 2 | 10 | 5.5 | 6 |
| O | 2.5 | 25 | 10 | 10 |
| P | 1.5 | 20 | 20 | 1 |

EXAMPLE 6

Samples of 100 g each of cotton creton are impregnated on a padder with a 1% solution of one of the compounds of the formula (1) in isopropanol at 20° C and then squeezed to a weight increase of 100%.

Samples of 100 g each of wool cheviot were treated in an identical manner.

After having been dried at 30° to 40° C the fabrics contain 1% of active substance referred to their own weight.

To test the activity against bacteria round blanks of 10 mm diameter of the impregnated fabrics, one half of which untreated and the other after having been watered for 24 hours at 29° C, are placed on brain infusion agar plates previously inoculated with Staphylococcus aureus. The plates are then incubated for 24 hours at 37° C.

To test the activity against fungi round blanks of 25 mm diameter are placed on beerwort agar plates and then inoculated with Aspergillus niger, and the plates are then incubated for 72 hours at 30° C.

The evaluation extends, on one hand, to the inhibitory zones (IZ in mm) around the blanks and, on the other hand, on the growth (G in %) detected under a microscope underneath and/or on the fabric:

| Microorganisms | Substrate (with 1% of active substance) | Active substance | untreated | | watered | |
|---|---|---|---|---|---|---|
| | | | IZ mm | G % | IZ mm | G % |
| Staphylococcus aureus | cotton | A | 6 | 0 | 5 | 0 |
| | | F | 3 | 0 | 2 | 0 |
| | | M | 5 | 0 | 2 | 0 |
| | wool | A | 6 | 0 | 3 | 0 |
| | | M | 4 | 0 | 1 | 0 |
| Aspergillus niger | cotton | A | 7 | 0 | 4 | 0 |
| | | M | 4 | 0 | 1 | 0 |
| | wool | A | 0 | 0 | 0 | 0 |
| | | M | 20 | 0 | 5 | 0 |

EXAMPLE 7

Crude paper, which consists of 90% of bleached sulphite cellulose and 10% of birch pulp, is impregnated in a sizing press with a 2.5% solution of the compound of the formula (11) in methanol+water 2:1 to a weight increase of 40%.

The dried paper contains 1% of active substance referred to its original weight.

To test its antibacterial properties round blanks of 10 mm diameter of the impregnated paper are placed on brain heart infusion agar plates previously inoculated with Staphylococcus aureus, and the plates are then incubated for 24 hours at 37° C.

For testing its fungicidal activity round blanks of 25 mm diameter are placed on Mycophil-Agar plates and inoculated with Aspergillus niger, and the plates are incubated for 72 hours at 30° C.

The evaluation extends, on one hand, to the inhibitory zone (IZ in mm) around the paper blanks and, on the other hand, to the microscopically discernible growth (G in %) underneath and/or on the blanks:

TABLE IV

| | IZ in mm | G in % |
|---|---|---|
| Staphylococcus aureus | 2.5 | 0 |
| Aspergillus niger | 1 | 0 |

What we claim is:

1. A quaternary ammonium-hydroxyaryl compound of the formula

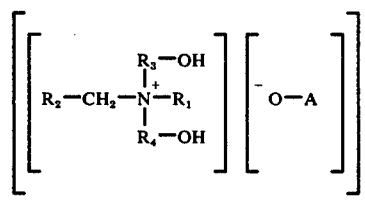

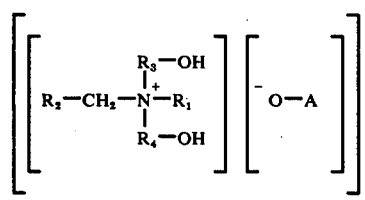 (1)

in which $R_1$ represents alkyl of 10 to 22 carbon atoms, $R_2$ represents phenyl or phenyl substituted by a member selected from the group consisting of halogen or alkyl of 1 to 4 carbon atoms, $R_3$ and $R_4$ each represents ethylene and A represents biphenyl, phenyl or a group of the formula

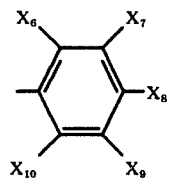

in which one to three of the $X_{6-10}$ represent halogen, at most two of the $X_{6-10}$ represent an alkyl of 1 to 4 carbon atoms and the remaining $X_{6-10}$ represents hydrogen.

2. A compound according to claim 1, wherein A corresponds to the formula

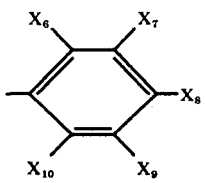

in which one of the $X_{6-10}$ represents halogen, at most two of the $X_{6-10}$ represents methyl, and the remaining $X_{6-10}$ represents hydrogen.

3. A compound according to claim 1, wherein A corresponds to the formula

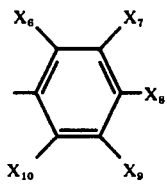

in which one to three of the $X_{6-10}$ represent halogen, at most two of the $X_{6-10}$ represent methyl and the remaining $X_{6-10}$ represent hydrogen.

4. A compound according to claim 1, wherein A corresponds to the formula

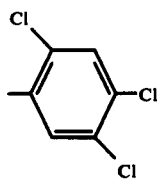

5. A compound according to claim 1, wherein $R_1$ represents an alkyl of 10 to 22 carbon atoms.

6. A compound according to claim 1, wherein $R_1$ represents an alkyl of 10 to 22 carbon atoms and $R_2$ represents a radical of the formula

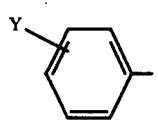

wherein Y stands for a member selected from the group consisting of a hydrogen atom, a halogen atom and a methyl group.

7. A compound according to claim 1, wherein $R_1$ represents an alkyl of 10 to 22 carbon atoms, $R_2$ represents a phenyl group and $R_3$ and $R_4$ represents a $-CH_2-CH_2-$ group.

8. A compound according to claim 1, wherein $R_1$ represents a $-(CH_2)_{11}-CH_3$ radical, $R_2$ represents a phenyl group, $R_3$ and $R_4$ each represents a $-CH_2-CH_2-$ group and A corresponds to the formula

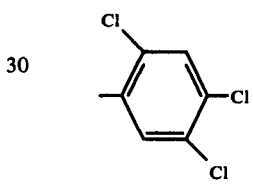

* * * * *

UNITED STATES PATENT OFFICE
CERTIFICATE OF CORRECTION

PATENT NO. : 4,025,556

DATED : May 24, 1977

INVENTOR(S) : Max Schellenbaum and Max Dünnenberger

It is certified that error appears in the above-identified patent and that said Letters Patent are hereby corrected as shown below:

Column 14, claim 1, lines 40-45, delete the structural formula (1) in its second occurrence.

Signed and Sealed this sixteenth Day of August 1977

[SEAL]

Attest:

RUTH C. MASON
*Attesting Officer*

C. MARSHALL DANN
*Commissioner of Patents and Trademarks*